United States Patent
Takeuchi et al.

(10) Patent No.: US 11,696,688 B2
(45) Date of Patent: Jul. 11, 2023

(54) SEMICONDUCTOR SWCNT SLURRY FOR BIOIMAGING AND METHOD FOR PRODUCING THE SAME

(71) Applicants: SHIMADZU CORPORATION, Kyoto (JP); NATIONAL INSTITUTE OF ADVANCED INDUSTRIAL SCIENCE AND TECHNOLOGY, Tokyo (JP)

(72) Inventors: Tsukasa Takeuchi, Kyoto (JP); Toshiya Okazaki, Ibaraki (JP); Yoko Iizumi, Ibaraki (JP); Hiromichi Kataura, Ibaraki (JP); Masako Yudasaka, Ibaraki (JP)

(73) Assignees: SHIMADZU CORPORATION, Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 183 days.

(21) Appl. No.: 16/764,250

(22) PCT Filed: Nov. 17, 2017

(86) PCT No.: PCT/JP2017/041562
§ 371 (c)(1),
(2) Date: May 14, 2020

(87) PCT Pub. No.: WO2019/097697
PCT Pub. Date: May 23, 2019

(65) Prior Publication Data
US 2020/0367754 A1 Nov. 26, 2020

(51) Int. Cl.
| | | |
|---|---|---|
| A61B 5/00 | (2006.01) | |
| C01B 32/159 | (2017.01) | |
| C01B 32/174 | (2017.01) | |
| H10K 85/20 | (2023.01) | |
| B82Y 5/00 | (2011.01) | |
| B82Y 40/00 | (2011.01) | |

(52) U.S. Cl.
CPC .......... *A61B 5/0071* (2013.01); *A61B 5/0086* (2013.01); *C01B 32/159* (2017.08); *C01B 32/174* (2017.08); *H10K 85/221* (2023.02); *B82Y 5/00* (2013.01); *B82Y 40/00* (2013.01)

(58) Field of Classification Search
CPC .............. A61B 5/0071; A61B 5/0086; C01B 32/159; C01B 32/174; H01L 51/0048; B82Y 5/00; B82Y 40/00; A61K 49/0065; H10K 85/221
USPC ........................................................ 600/431
See application file for complete search history.

(56) References Cited

U.S. PATENT DOCUMENTS

| | | | | |
|---|---|---|---|---|
| 6,692,717 B1* | 2/2004 | Smalley | ................ | C01B 32/162 |
| | | | | 423/445 B |
| 8,557,128 B2* | 10/2013 | Millward | .......... | H01L 21/02002 |
| | | | | 427/337 |
| 8,828,533 B2* | 9/2014 | Dai | ..................... | C04B 38/0032 |
| | | | | 252/502 |
| 9,506,194 B2* | 11/2016 | Schweiger | ............ | D04H 1/732 |
| 2008/0152593 A1 | 6/2008 | Iijima et al. | | |
| 2013/0004657 A1* | 1/2013 | Xu | .......................... | H01B 1/24 |
| | | | | 252/511 |
| 2017/0335185 A1 | 11/2017 | Iizumi et al. | | |
| 2020/0384127 A1* | 12/2020 | Takeuchi | ........... | A61K 49/0019 |

FOREIGN PATENT DOCUMENTS

| | | | | |
|---|---|---|---|---|
| CN | 106463710 A | * | 2/2017 | .......... H01M 10/052 |
| JP | 2006-182657 A | | 7/2006 | |
| JP | 2012-32358 A | | 2/2012 | |
| JP | 2015-11582 A | | 1/2015 | |
| WO | 2014/080519 A1 | | 5/2014 | |
| WO | 2016/117633 A1 | | 7/2016 | |

OTHER PUBLICATIONS

Umezawa et al., "Mouseairway imaging by using near-infrared fluorescent carbon nanotube", Bioimaging, vol. 25, No. 2, p. 123, 2016, 5 pages total.
Ghosh et al., "Oxygen Doping Modifies Near-Infrared Band Gaps in Fluorescent Single-Walled Carbon Nanotubes", Science, vol. 330, pp. 1656-1659, Dec. 17, 2010, 4 pages total.
Miyauchi et al., "Brightening of excitons in carbon nanotubes on dimensionality modification", Nature Photonics, vol. 7, pp. 715-719, Sep. 2013, 5 pages total.
International Search Report and Written Opinion dated Jan. 9, 2018 in Application No. PCT/JP2017/041562.
Notice of Reasons for Refusal dated Nov. 2, 2021 from the Japanese Patent Office in Japanese Application No. 2019-553647.
Joshua T. Robinson et al., "In Vivo Fluorescence Imaging in the Second Near-Infrared Window with Long Circulating Carbon Nanotubes Capable of Ultrahigh Tumor Uptake", Journal of the American Chemical Society, 2012, vol. 134, pp. 10664-10669 (6 pages total).
Communication dated May 30, 2022, issued in Chinese Application No. 201780096906.X.
Office Action dated Nov. 7, 2022 in Chinese Application No. 201780096906.X.

* cited by examiner

*Primary Examiner* — Douglas J Mc Ginty
(74) *Attorney, Agent, or Firm* — Sughrue Mion, PLLC

(57) ABSTRACT

An object is to provide an SWCNT slurry for bioimaging with reduced toxicity that causes no aggregation of semiconductor SWCNTs, no accumulation in a specific site when administered to a living organism, and no clogging in blood vessels such as those in the lungs. In order to achieve the above-described object, a semiconductor single-walled carbon nanotube (SWCNT) slurry for bioimaging according to the present invention includes: semiconductor SWCNTs having an average particle size of less than 10 nm; and a dispersant composed of an amphiphilic substance that coats the surfaces of the SWCNTs.

10 Claims, 2 Drawing Sheets

SEMICONDUCTOR SWCNT SLURRY FOR BIOIMAGING AND METHOD FOR PRODUCING THE SAME

CROSS REFERENCE TO RELATED APPLICATIONS

This application is a National Stage of International Application No. PCT/JP2017/041562, filed Nov. 17, 2017.

TECHNICAL FIELD

The present invention relates to a semiconductor single-walled carbon nanotube (SWCNT) slurry for bioimaging and a method for producing the same.

BACKGROUND ART

Carbon nanotubes (hereinafter, also referred to as CNTs) refer to a carbon structure having a structure in which a carbon sheet (what is known as a graphite sheet), having carbon atoms in hexagonal planer arrangement, is closed to be in a cylindrical form. The CNTs include multi-walled and single-walled CNTs. The single-walled CNTs (hereinafter, also referred to as SWCNTs) are known to have electronic properties depending on how they are wound (diameter and spiral degree), meaning that they exhibit either metallic property or semiconducting property.

Semiconductor SWCNTs absorb and emit light in a near-infrared region (800 to 2000 nm) with good biological penetration, and thus are expected to be useful as fluorescent probes for detecting the functions of cells and living organisms. In particular, the wavelength region of 1200 to 1400 nm is a region with the best biological penetration.

The emission wavelength can be changed by introducing oxygen atoms or functional groups into the semiconductor SWCNTs. For example, a technique is known in which water containing ozone is mixed with an aqueous solution in which SWCNTs are dispersed with a surfactant, and a chemical reaction is performed with light irradiation to partially replace carbon in the nanotube walls with oxygen atoms (Non Patent Literatures 1 and 2). When oxygen atoms are introduced in this manner, most of the oxygen atoms are ether-bonded to the walls of the SWCNTs, and the emission energy of the SWCNTs becomes about 150 meV smaller than the original emission energy. Such chemical modification also has the advantage of increasing the emission quantum yield of SWCNTs.

However, as for the longer emission wavelength reported in Non Patent Literatures 1 and 2, an SWCNT having a chiral index (6,5), which is one of the most studied SWCNTs at present, the emission wavelength having a peak at about 1140 nm (about 1.088 eV) is predominant. It is shorter than about 1300 nm to 1400 nm, which is known to be most preferred as near-infrared fluorescent probes.

Patent Literature 1 discloses a method for producing near-infrared light emitting semiconductor single-walled carbon nanotubes that includes irradiating semiconductor single-walled carbon nanotubes directly with ultraviolet rays in the atmosphere to generate ozone and oxidize the semiconductor single-walled carbon nanotubes.

According to the abovementioned Patent Literature 1, oxygen atoms can be easily introduced into the SWCNTs in the order of grams in a short time, and the emission wavelength peak can be changed from 980 nm (1.265 eV) to 1280±13 nm (0.9686±0.01 eV).

CITATION LIST

Patent Literature

Patent Literature 1: International Publication No. 2016/117633

Non Patent Literature

Non Patent Literature 1: Ghosh et al., Science, 330, 1656-1659 (2010).
Non Patent Literature 2: Miyauchi et al., Nat. Photonics, 7, 715-719 (2013).

SUMMARY OF INVENTION

Technical Problem

However, semiconductor SWCNTs manufactured by the method described in Patent Literature 1, when administered to a living organism (mouse) as a slurry for bioimaging (probe for living organisms), accumulate in a specific site (especially the liver) in a short period of time, cause halation in detecting a fluorescence distribution, and result in a failure to detect the fluorescence distribution in other regions. In addition, since semiconductor SWCNTs have high cohesiveness, there is a problem in that administering the SWCNTs to a living organism, such as a mouse, can lead to a risk that the SWCNTs may aggregate and clog in the lungs and the like, which could be fatal Furthermore, the aggregation of the semiconductor SWCNTs has a problem of reduced emission quantum efficiency of the semiconductor SWCNTs.

The present invention has been made in view of the above-mentioned conventional circumstances, and an object of the present invention is to provide an SWCNT slurry for bioimaging with reduced toxicity that causes no aggregation of semiconductor SWCNTs, no accumulation in a specific site when administered to a living organism, and no clogging in blood vessels such as those in the lungs, and to provide a method for producing the same.

Solution to Problem

As a result of intensive studies, the inventors of the present invention have found that coating a specific semiconductor SWCNT with an amphiphilic substance improves the dispersibility of the semiconductor SWCNT. The inventors of the present invention have also found that, in producing a semiconductor SWCNT slurry, by first dispersing semiconductor SWCNTs in a surfactant solution and then replacing the surfactant with a dispersant composed of an amphiphilic substance by dialysis, a semiconductor SWCNT slurry having excellent dispersibility can be obtained and thus completed the present invention. Specifically, the gist of the present invention is as follows.

(1) A semiconductor SWCNT slurry for bioimaging, comprising: semiconductor SWCNTs having an average particle size of less than 10 nm; and a dispersant composed of an amphiphilic substance that coats surfaces of the semiconductor SWCNTs.
(2) The semiconductor SWCNT slurry for bioimaging according to the above (1), wherein oxygen atoms are introduced as an epoxide into the semiconductor SWCNTs.
(3) The semiconductor SWCNT slurry for bioimaging according to the above (1) or (2), wherein the semiconductor SWCNTs have an emission wavelength peak in a wavelength region of 1200 nm or more to 1400 nm or less.

(4) The semiconductor SWCNT slurry for bioimaging according to the above (1), wherein the semiconductor SWCNTs are semiconductor SWCNTs oxidized by direct irradiation with ultraviolet rays in atmosphere.

(5) The semiconductor SWCNT slurry for bioimaging according to any one of the above (1) to (4), wherein the dispersant is a polyethylene glycol lipid derivative.

(6) A method for producing a semiconductor single-walled carbon nanotube (SWCNT) slurry for bioimaging according to the above (1), the method comprising:

a step of dispersing semiconductor SWCNTs having an average particle size of less than 10 nm in a surfactant solution;

a step of dissolving a dispersant composed of an amphiphilic substance in a resulting slurry; and a step of removing the surfactant from a resulting solution by dialysis.

(7) The method for producing a semiconductor SWCNT slurry for bioimaging according to the above (6), wherein oxygen atoms are introduced as an epoxide into the semiconductor SWCNTs.

(8) The method for producing a semiconductor SWCNT slurry for bioimaging according to the above (6) or (7), wherein the semiconductor SWCNTs have an emission wavelength peak in a wavelength region of 1200 nm or more to 1400 nm or less.

(9) The method for producing a semiconductor SWCNT slurry for bioimaging according to the above (6), wherein the semiconductor SWCNTs are semiconductor SWCNTs oxidized by direct irradiation with ultraviolet rays in atmosphere.

(10) The method for producing a semiconductor SWCNT slurry for bioimaging according to any one of the above (6) to (9), wherein the dispersant is a polyethylene glycol lipid derivative.

(11) The method for producing a semiconductor SWCNT slurry for bioimaging according to any one of the above (6) to (10), wherein the surfactant is sodium lauryl benzene sulfate.

Advantageous Effects of Invention

Since the semiconductor SWCNT slurry for bioimaging according to the present invention has a small particle size of the semiconductor SWCNTs, and its dispersion state is maintained by the dispersant, it does not accumulate in a specific organ (mainly, the liver), halation in detecting a fluorescence distribution can be reduced, and a decrease in the emitted fluorescence intensity can be prevented. In addition, the semiconductor SWCNT slurry causes no clogging in blood vessels such as those in the lungs and has extremely low toxicity. Specifically, semiconductor SWCNTs may be interspersed and held in gaps between cells, but do not cause toxicity.

In addition, in manufacturing a semiconductor SWCNT slurry for bioimaging, the surfactant is removed by dialysis and is replaced with a dispersant, whereby toxicity can be significantly reduced and the dispersibility of the semiconductor SWCNTs can be improved.

DESCRIPTION OF EMBODIMENTS

Figure 1:
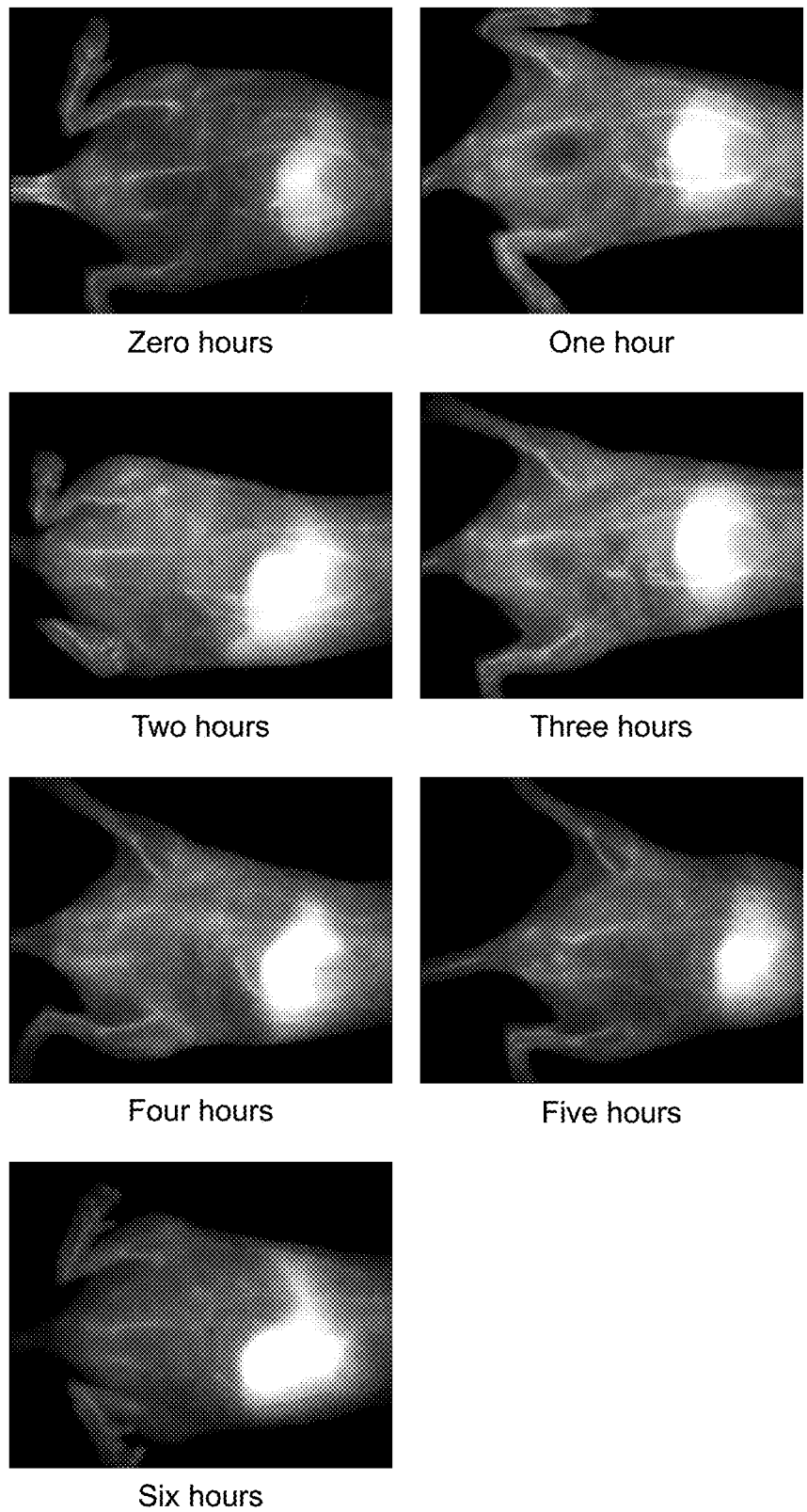
FIG. 1 is a view showing in vivo imaging in Example 1.

Hereinafter, the present invention will be described in detail.

A semiconductor SWCNT slurry for bioimaging according to the present invention includes semiconductor SWCNTs having an average particle size of less than 10 nm and a dispersant composed of an amphiphilic substance that coats the surfaces of the semiconductor SWCNTs.

Furthermore, it is preferable that the above-described semiconductor SWCNTs are subjected to an oxidation treatment by being directly irradiated with ultraviolet rays in the atmosphere. By direct irradiation with ultraviolet rays in the atmosphere, ozone is generated and oxygen atoms are introduced into the semiconductor SWCNTs. The semiconductor SWCNTs obtained by direct irradiation with ultraviolet rays in the atmosphere can shift the emission energy to the low energy side by 296±10 meV. Especially when applied to SWCNTs having a chiral index (6,5), the emission wavelength peak changes from about 980 nm to a wavelength region of 1200 nm or more to 1400 nm or less. Specifically, the emission wavelength peak changes to, for example, 1280±13 nm, and thus the emission wavelength has its peak in a wavelength region having biological penetration, which is preferable as a near-infrared fluorescent probe.

Regarding the oxidation treatment by irradiation with ultraviolet rays, in the conventional wet method (method for reacting SWCNTs in an aqueous solution) such as Non Patent Literatures 1 and 2 described above, most oxygen is ether-bonded with SWCNTs, and low energy shifts exceeding 290 meV is difficult. In contrast, when ultraviolet rays is directly irradiated in the atmosphere, most of the introduced oxygen atoms are introduced into SWCNTs as an epoxide, which enables a shift of the emission energy of the SWCNTs to the low energy side of 296±10 meV.

The method for synthesizing the semiconductor SWCNTs is not particularly limited, and the semiconductor SWCNTs can be synthesized as appropriate using a known method such as a chemical vapor deposition method, an arc discharge method, and a laser evaporation method. In particular, it is preferable to synthesize the semiconductor SWCNTs by a chemical vapor deposition method in the presence of a catalyst.

The average particle size of the semiconductor SWCNTs is smaller than 10 nm, and is preferably in the range of 6 nm or more and less than 10 nm. Micro semiconductor SWCNTs having an average particle size of less than 10 nm cause no clogging in blood vessels in the lungs and the like, and have low toxicity. Here, the average particle size of the semiconductor SWCNTs refers to an average diameter in a weight-based particle size distribution measured by a centrifugal sedimentation method.

To generate ozone by direct irradiation with ultraviolet rays in the atmosphere, it is preferable to perform the ozone generation in a closed space. For example, a device that generates ozone by irradiating the atmosphere with ultraviolet rays, such as a UV ozone cleaner, is preferably used. Irradiation conditions of ultraviolet rays vary depending on an apparatus used, and it is preferable that the irradiation is performed under conditions that the semiconductor SWCNTs are not destroyed by the irradiation.

In addition, in order to directly irradiate the semiconductor SWCNTs with ultraviolet rays in the atmosphere, it is preferable to previously form the semiconductor SWCNTs in a film state on a base material. In particular, in order to cause an even chemical reaction in the semiconductor SWCNTs into which oxygen atoms are introduced, it is preferable to irradiate the semiconductor SWCNTs formed into a thin film having a thickness of about 1 µm with ultraviolet rays.

The dispersant composed of an amphiphilic substance that coats the surfaces of the semiconductor SWCNTs is not particularly limited, and any dispersant may be used as appropriate as long as it has low toxicity to living organisms and has excellent affinity with the semiconductor SWCNTs. Specific examples include polyethylene glycol lipid derivatives in which hydrophilic PEG is bonded to a hydrophobic lipid site, nucleic acids, bovine serum albumin, and the like. In particular, polyethylene glycol lipid derivatives such as distearoyl-phosphatidylethanolamine-PEG2000 (DSPE-$PEG_{2000}$) are preferably used.

By coating the surfaces of the semiconductor SWCNTs with a dispersant such as DSPE-$PEG_{2000}$, the dispersion state of the semiconductor SWCNTs is maintained. In addition, the semiconductor SWCNTs have a micro particle size. Thus, the semiconductor SWCNTs cause no accumulation in a specific organ or no clogging in blood vessels of the lungs and the like.

The weight ratio of the oxidized semiconductor SWCNTs to the dispersant composed of an amphiphilic substance is not particularly limited as long as the surfaces of the semiconductor SWCNTs is sufficiently coated and the dispersion state can be maintained. It is preferable that the weight ratio of the oxidized semiconductor SWCNTs to the dispersant is in the range of 1:2 to 1:20.

To produce the semiconductor SWCNT slurry for bioimaging as described above, first, as described above, it is preferable to disperse semiconductor SWCNTs, oxidized by direct irradiation with ultraviolet rays in the atmosphere and having an average particle size smaller than 10 nm, in a surfactant solution.

Here, the surfactant may be any one that can disperse the semiconductor SWCNTs, and can be selected for use from various known surfactants such as an anionic surfactant, a cationic surfactant, an amphoteric ionic surfactant, and a nonionic surfactant.

Examples of the anionic surfactant include alkyl benzene sulfonate, alkyl naphthalene sulfonate, alkyl sulfonate, dialkyl sulfosuccinate, alkyl sulfate, polyoxyethylene alkyl ether sulfate, alkyl phosphate, polyoxyethylene alkyl ether phosphate, cholate, deoxycholate, glycocholate, taurocholate, and taurodeoxycholate.

Examples of the cationic surfactant include tetraalkylammonium salts, trialkylbenzylammonium salts, and alkylpyridinium salts.

Examples of the amphoteric surfactants include ampoteric polymers such as 2-methacryloyloxyphosphorylcholine polymers and polypeptides, 3-(N,N-dimethylstearylammonio)-propanesulfonate, 3-(N,N-dimethylstearylammonio) propanesulfonate, 3-(N,N-dimethylmyristylammonio) propanesulfonate, 3-[(3-cholamidopropyl) dimethylammonio] propanesulfonate (CHAPS), 3-[(3-cholamidopropyl) dimethylammonio]-2-hydroxypropanesulfonate (CHAPSO), n-dodecyl-N,N'-dimethyl-3-ammonio-1-propanesulfonate, n-hexadecyl-N,N'-dimethyl-3-ammonio-1-propanesulfonate, n-octylphosphocholine, n-dodecylphosphocholine, n-tetradecylphosphocholine, n-hexadecylphosphocholine, dimethylalkyl betaine, perfluoroalkyl betaine, and N,N-bis(3-D-gluconamide propyl)-cholamido, and lecithin.

Examples of the nonionic surfactant include polyoxyethylene alkyl ether, polyoxyethylene alkyl phenyl ether, polyoxyethylene polyhydric alcohol fatty acid partial ester, and polyglycerin fatty acid ester.

In particular, alkylbenzene sulfonates such as sodium lauryl benzenesulfate (SDBS) are preferably used because of their excellent dispersibility for semiconductor SWCNTs.

As a method for dispersing the semiconductor SWCNTs in a surfactant solution, various kinds of homogenizers and the like can be used.

The obtained slurry may be subjected to centrifugation as necessary, and the supernatant is collected, so that the isolated dispersibility of the semiconductor SWCNTs can be enhanced. The isolated and dispersed semiconductor single-walled SWCNTs are preferable because they have advantages of improvement in fluorescence quantum efficiency, observability, and clearance when administered to living organisms.

Subsequently, a dispersant composed of an amphiphilic substance, such as the above-mentioned polyethylene glycol lipid derivatives, is dissolved in the slurry obtained by dispersing the semiconductor SWCNTs in the surfactant solution, and thereafter, the surfactant is removed from the resulting solution by dialysis. As a result, the surfactant existing around the semiconductor SWCNTs is replaced with a dispersant such as a polyethylene glycol lipid derivative, and the surfaces of the semiconductor SWCNTs is coated with the dispersant.

When the semiconductor SWCNTs whose surface is coated with the dispersant are administered to a living organism as a semiconductor SWCNT slurry for bioimaging, the dispersion state is maintained. In addition, the semiconductor SWCNTs have a micro particle size. Thus, the semiconductor SWCNTs cause no accumulation in a specific organ (mainly the liver), whereby halation can be reduced. In addition, the semiconductor SWCNTs cause no clogging in blood vessels of the lungs and the like, and the surfactant such as SDBS and the like is removed by dialysis, whereby the toxicity is extremely low. In addition, since the semiconductor SWCNTs are dispersed well, their cohesiveness is reduced, whereby a decrease in the emitted fluorescence intensity can be prevented.

EXAMPLES

Hereinafter, the present invention will be described in more detail based on an example and a comparative example, but the present invention is not limited to these examples.

Example 1

To 10 ml of ethanol, 1 mg of carbon nanotubes (CoMo-CAT SG65i, average diameter 0.8 nm, hereinafter referred to as "semiconductor SWCNTs") was added, and the semiconductor SWCNTs were dispersed in ethanol by bath sonication for about 5 minutes. Subsequently, an omnipore membrane (φ47 mm, 5 µm pore) was set in a reduced pressure filter, a semiconductor SWCNT/ethanol slurry was put therein and filtered, and the semiconductor SWCNTs were uniformly placed on the filter. Next, the semiconductor SWCNTs remaining on the filter were placed in between sheets of medical paper, and dried at 60° C. for 30 minutes while being weighted lightly so that the filter was not rolled up. Then, the semiconductor SWCNTs placed on the filter were ozone-treated together with the filter for 60 to 70 seconds (the light source was a mercury lamp, and the ultraviolet intensity on the semiconductor SWCNTs was about 19 mW/cm$^2$).

After the ozone treatment, the semiconductor SWCNTs together with the filter were put in 10 ml of 1% SDBS-H$_2$O and sonicated for 20 minutes (ON:OFF=1 second:1 second) while being cooled with ice using a tip-type homogenizer, whereby the semiconductor SWCNTs were dispersed in the SDBS solution. Subsequently, the semiconductor SWCNT slurry from which the filter was removed was applied to an ultracentrifuge (104,000 g, 3 hours), and the supernatant was collected to obtain a semiconductor SWCNT isolated slurry.

Distearoyl phosphatidylethanolamine-PEG2000 (DSPE-PEG$_{2000}$) was added to the semiconductor SWCNT isolated slurry at a concentration of 3 mg/ml, and the powder of DSPE-PEG$_{2000}$ was dissolved by bath sonication for about 5 minutes. Then, this solution was put into a dialysis membrane (Spectrum, G235070), and dialyzed against 2 liters of water. In this process, SDBS was replaced with DSPE-PEG$_{2000}$.

Two hours later, 5 ml of the external dialysate was set aside for analysis and the remaining dialysate was discarded and replaced with water. Similarly, after one night, two days, and three days, the water was replaced with new one, and the dialysis rate was calculated by measuring the absorption spectrum of the external dialysate set aside for analysis. The dialysis was ended when the elution of SDBS of 95% or more was observed.

Finally, the absorption spectrum and the PL spectrum of the semiconductor SWCNT/DSPE-PEG$_{2000}$ slurry were measured to confirm that there was no aggregation of CNTs or quenching. Then, an intended semiconductor SWCNT slurry for bioimaging was produced. Measurement of the particle size of the semiconductor SWCNT slurry for bioimaging by the centrifugal sedimentation method revealed that the average particle size of the semiconductor SWCNTs in the slurry was 6.5 nm.

Comparative Example 1

To 10 ml of ethanol, 1 mg of carbon nanotubes (CoMo-CAT SG65i, average diameter 0.8 nm, hereinafter referred to as "semiconductor SWCNTs") was added, and the semiconductor SWCNTs were dispersed in ethanol by bath sonication for about 5 minutes. Subsequently, an omnipore membrane (φ47 mm, 5 μm pore) was set in a reduced pressure filter, a semiconductor SWCNT/ethanol slurry was put therein and filtered, and the semiconductor SWCNTs were uniformly placed on the filter. Next, the semiconductor SWCNTs remaining on the filter were placed in between sheets of medical paper, and dried at 60° C. for 30 minutes while being weighted lightly so that the filter was not rolled up. Then, the semiconductor SWCNTs placed on the filter were ozone-treated together with the filter for 60 to 70 seconds (the light source was a mercury lamp, and the ultraviolet intensity on the semiconductor SWCNTs was about 19 mW/cm$^2$).

After the ozone treatment, the semiconductor SWCNTs together with the filter were put in 10 ml of 0.3% distearoylphosphatidylethanolamine-PEG2000 (DSPE-PEG$_{2000}$) and sonicated for 20 minutes (ON:OFF=1 second:1 second) while being cooled with ice using a tip-type homogenizer, whereby the semiconductor SWCNTs were dispersed in the DSPE-PEG$_{2000}$ solution. Subsequently, the semiconductor SWCNT slurry from which the filter was removed was subjected to an ultracentrifuge (104,000 g, 3 hours), and the supernatant was collected. Finally, the absorption spectrum and the PL spectrum of the semiconductor SWCNT/DSPE-PEG$_{2000}$ slurry were measured to confirm that there was no aggregation of CNTs or quenching. Then, a semiconductor SWCNT slurry for bioimaging in the comparative example was produced. Measurement of the particle size of the semiconductor SWCNT slurry for bioimaging by the centrifugal sedimentation method revealed that the average particle size of the semiconductor SWCNTs in the slurry was 8 nm.

(In Vivo Imaging)

To mice, 0.1 ml of the semiconductor SWCNT slurry for bioimaging obtained in Example 1 and Comparative Example 1 was administered, and the fluorescence after 0 to 6 hours was observed using the SAI-1000 apparatus manufactured by Shimadzu Corporation. The results are shown in FIG. 1 (Example 1) and FIG. 2 (Comparative Example 1).

Figure 2:
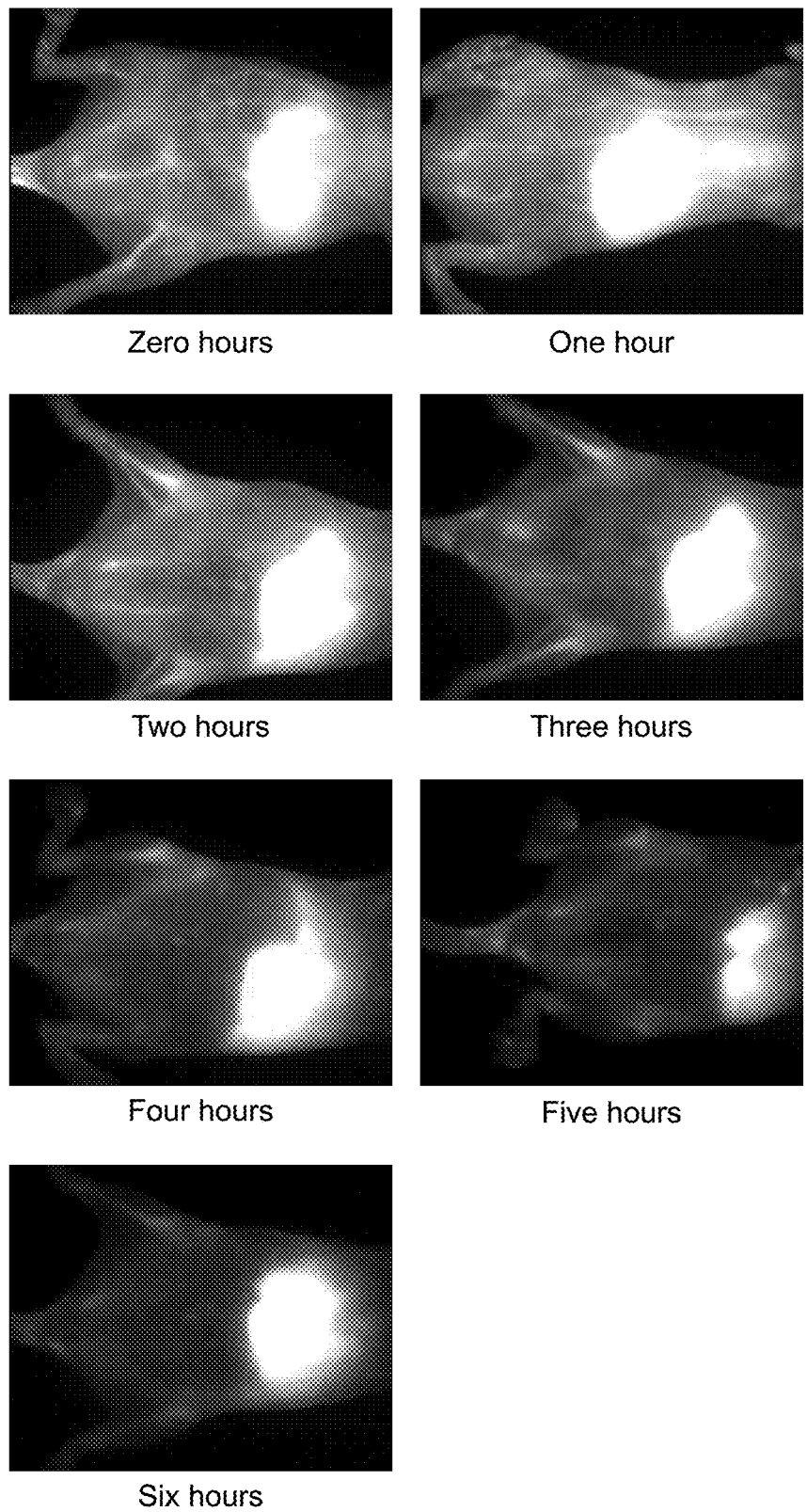
FIG. 2 is a view showing in vivo imaging in Comparative Example 1.

As shown in FIGS. 1 and 2, it is clear that the semiconductor SWCNT slurry in Example 1 is less likely to accumulate in a specific organ even after a lapse of time after administration as compared with Comparative Example 1, and can thus reduce halation. This is thought to be because Comparative Example 1 does not include the process of dispersing the semiconductor SWCNTs in a solution of a surfactant (SDBS), and thus the isolated dispersibility was low, the coating with DSPE-PEG$_{2000}$ was insufficient, and the semiconductor SWCNTs were not dispersed well and partially aggregated.

All publications, patent publications, and patent applications cited herein are hereby incorporated by reference in their entirety.

The invention claimed is:

1. A semiconductor single-walled carbon nanotube (SWCNT) slurry for bioimaging, comprising:
    semiconductor SWCNTs having an average particle size of less than 10 nm; and
    a dispersant composed of an amphiphilic substance that coats surfaces of the semiconductor SWCNTs;
    wherein the semiconductor SWCNTs have an emission wavelength peak in a wavelength region of 1200 nm or more to 1400 nm or less.

2. The semiconductor SWCNT slurry for bioimaging according to claim 1, wherein oxygen atoms are introduced as an epoxide into the semiconductor SWCNTs.

3. The semiconductor SWCNT slurry for bioimaging according to claim 1, wherein the semiconductor SWCNTs are semiconductor SWCNTs oxidized by direct irradiation with ultraviolet rays in atmosphere.

4. The semiconductor SWCNT slurry for bioimaging according to claim 1, wherein the dispersant is a polyethylene glycol lipid derivative.

5. A method for producing a semiconductor single-walled carbon nanotube (SWCNT) slurry for bioimaging according to claim 1, the method comprising:
    a step of dispersing semiconductor SWCNTs having an average particle size of less than 10 nm in a surfactant solution;
    a step of dissolving a dispersant composed of an amphiphilic substance in a resulting slurry; and
    a step of removing the surfactant from a resulting solution by dialysis.

6. The method for producing a semiconductor SWCNT slurry for bioimaging according to claim 5, wherein oxygen atoms are introduced as an epoxide into the semiconductor SWCNTs.

7. The method for producing a semiconductor SWCNT slurry for bioimaging according to claim 5, wherein the semiconductor SWCNTs have an emission wavelength peak in a wavelength region of 1200 nm or more to 1400 nm or less.

8. The method for producing a semiconductor SWCNT slurry for bioimaging according to claim 5, wherein the semiconductor SWCNTs are semiconductor SWCNTs oxidized by direct irradiation with ultraviolet rays in atmosphere.

9. The method for producing a semiconductor SWCNT slurry for bioimaging according to claim 5, wherein the dispersant is a polyethylene glycol lipid derivative.

10. The method for producing a semiconductor SWCNT slurry for bioimaging according to claim 5, wherein the surfactant is sodium lauryl benzene sulfate.

\* \* \* \* \*